United States Patent [19]

Stockburger

[11] Patent Number: 5,551,295
[45] Date of Patent: Sep. 3, 1996

[54] METHOD AND APPARATUS USING ULTRASONIC AND LIGHT WAVES FOR IDENTIFICATION OF TEST SPECIMENS

[76] Inventor: Hermann Stockburger, Hebelweg 13, Badenweiler D-7847, Germany

[21] Appl. No.: 362,555

[22] PCT Filed: Jun. 29, 1993

[86] PCT No.: PCT/EP93/01659

§ 371 Date: Jan. 25, 1995

§ 102(e) Date: Jan. 25, 1995

[87] PCT Pub. No.: WO94/01043

PCT Pub. Date: Jan. 20, 1994

[30] Foreign Application Priority Data

Jul. 8, 1992 [DE] Germany .......................... 42 22 387.3

[51] Int. Cl.⁶ .............................. G01N 29/26; G06K 9/00
[52] U.S. Cl. ............................. 73/602; 382/124; 356/71; 73/627
[58] Field of Search ............................. 382/124; 356/71; 73/602, 627, 629, 644, 601

[56] References Cited

U.S. PATENT DOCUMENTS

| 4,011,748 | 3/1977 | Bond et al. | 73/601 |
|---|---|---|---|
| 4,265,122 | 5/1981 | Cook et al. | 73/644 |
| 4,977,601 | 12/1990 | Biez | 382/124 |
| 5,224,174 | 6/1993 | Schneider | 73/602 |
| 5,241,606 | 8/1993 | Horie | 382/124 |
| 5,258,922 | 11/1993 | Grill | 73/602 |

FOREIGN PATENT DOCUMENTS

| 0048489 | 3/1982 | European Pat. Off. . |
|---|---|---|
| 0052349 | 5/1982 | European Pat. Off. . |
| 0402779 | 12/1990 | European Pat. Off. . |
| 3610397 | 10/1987 | Germany . |
| 4016105 | 12/1990 | Germany . |
| WO-A9209049 | 5/1992 | WIPO . |

*Primary Examiner*—Hezron E. Williams
*Assistant Examiner*—Rose M. Finley
*Attorney, Agent, or Firm*—Panitch Schwarze Jacobs & Nadel, P.C.

[57] ABSTRACT

The invention relates to a method and an apparatus for determining the authenticity and/or for identifying the respective spatial structure of a test specimen. The test specimen is placed on a surface and is exposed to ultrasonic waves traversing a body contiguous with the surface and the waves reflected and/or backscattered by the test specimen reproduce a different structure for different test specimens which are evaluated. It is characteristic of the method according to the invention that provided in the body (4) is a layer or surface (6) which is transparent to the ultrasonic waves and reflects and/or diffracts electromagnetic waves, that the layer or surface (6) in the body (4) is deformed in a locally different and time-dependent way by the ultrasonic waves according to the form and intensity of the backscattered or diffracted ultrasonic waves, and that the layer (6) is exposed to radiation of electromagnetic waves at an angle and in the area of the electromagnetic beams reflected and/or diffracted at the angle of emergence (9) the same are intercepted and their change caused by their reflection or diffraction at the layer (6) is evaluated. To carry out this method, the apparatus according to the invention is formed with the layer (6) arranged in the body (4) and the apparatus (1) has an electromagnetic radiation source (7), the beams of which are directed to the layer (6), and that at least one beam receiver (8) is provided in the area of the reflected or diffracted electromagnetic beam and serves to evaluate the beam (single FIGURE).

17 Claims, 1 Drawing Sheet

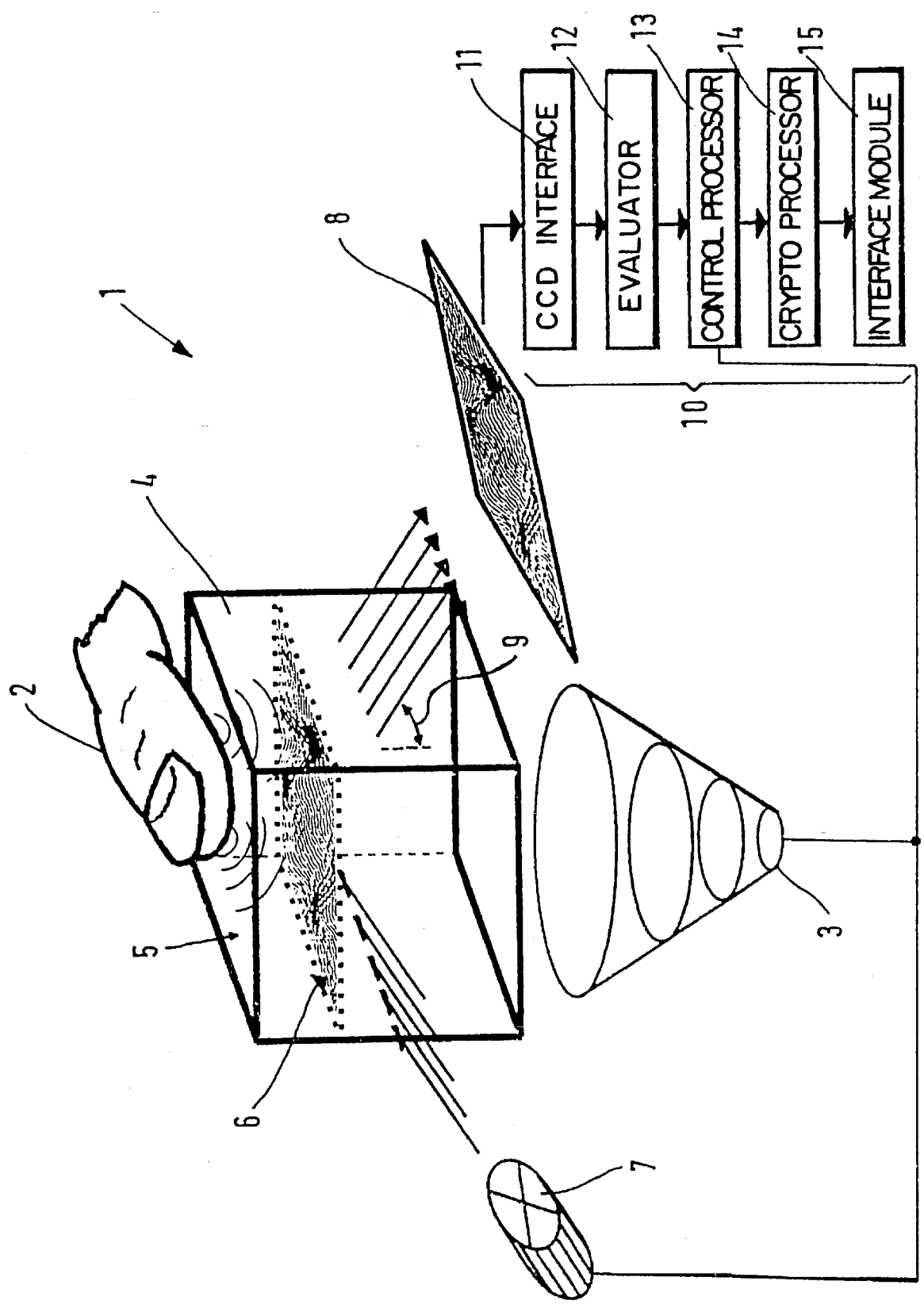

METHOD AND APPARATUS USING ULTRASONIC AND LIGHT WAVES FOR IDENTIFICATION OF TEST SPECIMENS

The invention relates to a method for determining the authenticity and/or for identifying the respective spatial structure of a test specimen, particularly the epithelial structure of the skin e.g. of a human finger, whereby this test specimen is placed on a plane or curved surface and is exposed to ultrasonic waves traversing a body contiguous with said surface and the ultrasonic waves reflected and/or backscattered at the test specimen reproduce a different structure in each case of different test specimens and are evaluated.

Such a method is known from German laid open print No. 40 16 105. Definite identification of individuals is possible because the epithelial structures vary significantly from person to person through the specific genetic code and the individual growth phases. In this method the reflected and scattered ultrasonic waves are intercepted by receivers, so that as large a number as possible of receivers is necessary for determining authenticity or identifying accurately. Since these require a corresponding amount of space, the method is unsuited for the authenticity of, for instance, the epithelial structure of a finger to be quickly checked in a cash dispenser, for example. If the number of receivers is reduced so as to make do with the space, sufficient single data can no longer be received to confidently recognize the individuality of the respective epithelial structure according to the finger placed and to distinguish it from another finger.

The object underlying the invention is therefore to provide a method of the kind mentioned at the outset, enabling high resolution of such a structure with moderately priced means, in the minimum of space.

The object is accomplished in that provided in the body is a layer or surface which is transparent to the ultrasonic waves and reflects and/or diffracts electromagnetic waves, that said layer or surface in the body is deformed in a locally different and time-dependent way by the ultrasonic waves according to the form and intensity of the backscattered or diffracted ultrasonic waves, and that said layer is exposed to radiation of electromagnetic waves at an angle, and in the area of the electromagnetic beams reflected and/or diffracted at the angle of emergence the same are intercepted and their change caused by their reflection or diffraction at the layer is evaluated.

The structures in the test specimen, in particular in the epithelial tissue of the human finger, cause a diffraction of the impinging ultrasonic wave when the ultrasonic wavelength is suitably selected. The diffracted, returning ultrasonic wave causes distortions or deformations in the body and on the layer. Since this layer has the property of reflecting or diffracting electromagnetic waves, the deformation structures on the layer can be optically detected. For instance, so-called CCD-arrays with several thousands of detector elements of matrix-like arrangement may be used as detectors, resulting in a high local resolution and high detection sensitivity with detectors available at moderate price.

It is suitable if the wavelength of the ultrasonic source is selected according to the size of the structures to be identified. Diffraction of the ultrasonic wave at the respective structures thereby occurs.

It is suitable if at least one detector is provided for evaluation of the reflected and/or diffracted electromagnetic beam, preferably of the light, and measures over a selected duration.

Through the evaluation within one time slot one obtains a snapshot of the reflected beam, through measurement within successive time slots separate in time one obtains a time-resolved "film" of the dynamically changing, reflected beam.

It is advantageous if the reflecting and/or diffractive layer in the beam path of the ultrasonic waves is arranged approximately perpendicular to the propagation direction of the ultrasonic waves and the electromagnetic waves are reflectively irradiated at the transition between body and reflecting layer.

The measuring system is simplified by the ultrasonic wave wave front traversing the layer frontally. Through the reflective property of the layer, optoelectronic methods can be used.

It is suitable if the exposure of the test specimen to ultrasonic waves traversing the body is periodically interrupted, the interruptions being determined in such a way that, at least intermittently, beams travel only in the direction of transmission or in the direction of reflection. By this means disturbances in measurement due to interferences between incoming and backscattered ultrasonic wave can be avoided.

It is suitable if within an ultrasonic pulse a plurality of ultrasonic wavelengths are traversed, particularly consecutively in time, and if these wavelengths are coordinated to the size of the structures to be identified. By this means structures differing greatly in size can be measured and identified.

To achieve the greatest possible local resolution it is suitable if the reflected and/or diffracted electromagnetic beams are imaged on the detector(s). In order that the electromagnetic beam neither over illuminates the surface formed by a plurality of detectors, whereby information would be lost, nor under-illuminates the surface present, whereby the maximum resolution would not be attained, the beam can be adapted by a lens system and imaged on the detectors.

An additional possibility for analysis ensues if, depending on the deformation of the reflecting and/or diffractive layer, white light impinging thereon is spectrally decomposed.

It is advantageous for evaluation if the data thus gained are compressed or certain data of the entire dataset are selected, coded and stored on a data carrier serving as reference for current measurements. This can be used to determine the respective test specimen, because every body penetrated by radiation can have different structures, the effects of which on the reflecting layer are orders of magnitude less though than those of the body to be identified. Above all, however, the individual epithelial structure data gained from a body to be identified can be stored on a data carrier and/or in a data base in order to be available at any time as reference, when the person whose finger was analysed has to be identified or verified, such as when a cash dispenser is used.

The invention further relates to an apparatus for carrying out the method, including at least one ultrasonic source, a body penetrable to radiation thereby and a supporting surface for the test specimen, the supporting surface being arranged at a fixed angle to the beam path of the ultrasonic source.

The apparatus according to the invention is characterized in that arranged in the body, beneath the supporting surface for the test specimen, is a layer reflecting and/or diffracting electromagnetic waves, and that said apparatus has a radiation source for electromagnetic waves, preferably a light source, the beams of which are directed to the layer and that at least one beam receiver is provided in the area of the reflected and/or diffracted beam and serves to evaluate the changes of this beam caused by the reflection or diffraction.

Through the reflective property, an instantaneous diffraction pattern formed on the layer can be optically read out.

It is suitable if the layer is arranged closely beneath and approximately parallel to the supporting surface and approximately at right angles to the path of the ultrasonic waves.

The measuring system is simplified by the ultrasonic wave fronts traversing the supporting surface and the layer frontally.

A suitable embodiment may consist in that the layer is a mirror layer, allowing particularly good reflective properties to be attained. It is also possible for a plurality of preferably parallel, reflecting surfaces or layers to be provided.

It is suitable if a plurality of detectors are arranged preferably in a matrix-like manner, the normal to the surface thereof running approximately parallel to the emergence angle of the electromagnetic beam. Thereby moderately priced, so-called CCD-arrays with high local resolution can be used.

It is suitable if the ultrasonic source is coupled to at least one pulser or the like. Thereby the ultrasonic source can be pulsed. The intervals between the successive pulses are to be set in such a way that interferences liable to disturb measurement are avoided within the body between incoming and backscattered wave.

It is particularly advantageous if at least one projector lens or the like is arranged in the beam path of the reflected and/or diffracted electromagnetic beams between the body and the beam receiver(s). By this means the beam obtains a diameter adapted to the detector surface present. The local resolution can be increased through this image formation.

Focussing on the detectors can be achieved if the reflecting and/or diffractive layer is curved. The curvature can act like a concave mirror.

An exemplary embodiment of the invention with its details of material importance will be described in closer detail below with reference to the drawing. The individual features may be realized singly or severally in an embodiment of the invention.

The single figure shows in schematic form a perspective view of the apparatus with body and test specimen during a measurement, the reflecting or diffractive layer or surface situated in the body being dynamically deformed in accordance with the diffraction pattern of the test specimen.

An apparatus generally designed 1 in FIG. 1 serves to determine the authenticity and/or to identify the respective spatial structure of a test specimen 2—e.g. the epithelial structure of the skin, particularly of a human finger. The apparatus has a body 4 penetrable by radiation of an ultrasonic source 3 and transparent to electromagnetic waves, a supporting surface 5 for the test specimen 2 being arranged on that side of the body 4 which faces away from the ultrasonic source 3. Arranged within the body 4, closely beneath this supporting surface 5, is a reflecting or diffractive layer 6 which is approximately parallel to the supporting surface 5 and forms an approximately right angle to the path of the ultrasonic waves emitted by the ultrasonic source 3. The body 4 and internal layer 6, which are both transparent to ultrasonic waves, are approximately the same in their elastic constants to limit the scatter losses of the sound waves at the layer 6.

The apparatus 1 furthermore has an electromagnetic radiation source 7,—in the exemplified embodiment a light source—the beams thereof penetrating the optically transparent body 4 at the side and therein impinging on the layer 6 at an angle. Since the layer 6 has a refractive index different from the body 4, the electromagnetic beams impinging the layer 6 are reflected at the emergence angle 9, leave the body 4 and are intercepted by a detector arrangement 8 connected to an evaluator 10.

To measure the structure to be analysed of a test specimen 2, particularly the epithelial structure of the skin e.g. of the finger, the finger is placed upon the finger application surface 5 of the body 4. The sound waves emitted by the ultrasonic source 3 pass through the body 4, the wave fronts traversing the layer 6 approximately frontally, and through the supporting surface 5 defining the body 4 they reach the uppermost dermal layers of the finger resting upon the supporting surface 5.

Individual structures of the epithelial tissue under the outermost dermal layer have extents lying in the order of magnitude of the wavelength of high-frequency ultrasound. They cause the ultrasonic waves impinging them to be diffracted and backscattered. On the basis of the diffraction effects brought about by the epthelial tissue, the diffracted ultrasonic wave returning to the body 4 has locally varying pressure amplitudes there and deforms the layer 6 in the body 4 in a locally different and time-dependent way according to the form and intensity of the returning, diffracted ultrasonic wave, as indicated in FIG. 1.

Since the layer 6, preferably a mirror layer, is exposed to radiation at an angle by the light source, the impinging electromagnetic beams are reflected at the angle of emergence 9 in accordance with the deformations which the layer presents at different angles with varying distribution of intensity.

Preferably a plurality of detectors 8 are arranged, particularly in matrix-like manner, in the area of these angles of scattering or reflection, the normal to the surface of this detector matrix running approximately parallel to the angle of emergence 9 of the light beam. This may be a so-called "CCD-array" (charge coupled device) with several thousands of detector elements, with the aid of which the local changes of the light beam caused by the reflection can be measured. In order that the reflected light beam illuminates the detector surface 8 virtually fully so as the achieve the greatest possible local resolution, a projector lens or the like may be arranged in the beam path of the light between the body 4 and the detectors 8 and images the reflected beam on the detectors 8 accordingly.

An advantageous embodiment of the device 1 consists in that the exposure of the test specimen 2 to ultrasonic waves traversing the body 4 is periodically interrupted, in particular the ultrasonic source 3 is coupled to a pulser (not shown) or the like. The intervals of interruption are determined in such a way that, at least intermittently, the ultrasonic waves travel only in the one or other direction backscattered by the test specimen. By this means disturbances in measurement due to interferences between incoming and returning ultrasonic wave are practically precluded. In order to generate diffraction effects, the wavelength of the ultrasonic source 3 is selected according to the size of the structures to be identified. Since, however, structures of varying size are to be detected, within an ultrasonic pulse a plurality of discrete ultrasonic wavelengths are traversed, these wavelengths corresponding approximately to the sizes of the varying structures. A wideband ultrasonic source (so-called "transducer") can also be used for this.

The detector arrangement 8, with which the distribution of intensity of the incident electromagnetic radiation is measured, is connected to an electronic evaluation and control unit, generally designated 10, where the measured data are temporarily stored and coded according to the different sound frequencies used and are stored on a data carrier. The evaluation includes image processing methods, such as Fourier transformation for instance. The stored data are then available as reference for current measurements. The control processor 13 is coupled to the ultrasonic source 3 and its pulser and determines the pulse lengths, the intervals of interruption and the frequency response. In the exemplified embodiment the electronic evaluation and control unit 10 consists of a CCD interface 11, an intelligent electronic evaluator 12, a control processor 13, a cryptoprocessor 14 for data coding and an interface module 15 for networking with various data bases or terminals.

Definite identification and/or verification of individuals is possible because the epithelial structures vary sigificantly from person to person through the specific genetic code and the individual growth phases. Tests have shown that with this method all test persons could be definitely identified and distinguished from one another by the skin e.g. of their finger.

In summary it should also be stated that the method of measurement is based on diffractive local resolution of individual structures of a test specimen 2 by means of ultrasound. Since the ultrasonic waves are selected in the order of magnitude of the structures to be resolved or somewhat smaller—owing to the high contrast—the backscattered ultrasonic wave is diffracted in different diffraction angles of varying intensity and phase position. The diffracted ultrasonic wave causes local, time-dependent deformations in the body 4 and in the layer 6, according to the diffraction pattern. Through optical reflection at these time-dependent deformations of this layer 6, the information varying over time can be read out optoelectronically.

The body 4 is made of glass of special acoustic and optical quality. Instead of a solid body, hollow bodies filled with suitably selected liquids can also be used. The layer 6 can be provided in a solid body 4 as follows. The body 4 is separated at a distance approximately parallel to the supporting surface 5 and the layer 6 can be applied or vapour-deposited for instance by photochemical or epitactic processes. The separated part of the body can then be restored to this layer by means of physical-chemical methods. Complete manufacture of the body 4 with the internal layer 6 is however also possible by epitactic methods. By this means material-specific deviations between these bodies 4 could also be kept small.

I claim:

1. A method for determining the authenticity and for identifying the respective spatial structure of a test specimen (2), particularly the epithelial structure of the skin, comprising the steps of:

providing a body (4) having a layer (6), which is transparent to ultrasonic waves and reflects electromagnetic waves, and a surface (5) for supporting the test specimen (2);

placing the test specimen (2) on the surface;

exposing the test specimen (2) to ultrasonic waves traversing the body (4) contiguous with said surface (5) such that the ultrasonic waves are reflected or backscattered by the test specimen (2);

deforming the layer (6) in the body (4) in a locally different and time-dependent way by the ultrasonic waves according to the form and intensity of the backscattered or reflected ultrasonic waves;

exposing said layer (6) to radiation of electromagnetic waves at an angle;

intercepting the electromagnetic waves reflected at an angle of emergence (9) from the layer (6); and evaluating a change in the reflected electromagnetic waves caused by their reflection at the layer (6).

2. A method as claimed in claim 1, further comprising the step of:

selecting a wavelength for the ultrasonic waves according to the size of the structure of the specimen to be identified.

3. A method as claimed in claim 1, further comprising the step of:

providing at least one detector (8) for evaluation of the reflected electromagnetic waves which measures over a selected duration.

4. A method as claimed in claim 1, further comprising the steps of:

arranging the layer (6) in a beam path of the ultrasonic waves approximately perpendicular to the propagation direction of the ultrasonic waves; and reflectively irradiating the electromagnetic waves at the transition between body (4) and reflecting layer (6).

5. A method as claimed in claim 1, further comprising the step of:

periodically interrupting exposure of the test specimen (2) to the ultrasonic waves traversing the body (4), with the periodic interruptions being determined in such a way that, at least intermittently, beams of ultrasonic waves travel only in one of a direction of transmission and a direction of reflection.

6. A method as claimed in claim 1, further comprising the step of:

providing a plurality of ultrasonic wavelengths within an ultrasonic pulse, particularly consecutively in time and such that said wavelengths are coordinated to the size of the structure to be identified.

7. A method as claimed in claim 1 further comprising the step of:

imaging the reflected electromagnetic waves on a detector (8).

8. A method as claimed in claim 1 wherein the electromagnetic waves are white light, further comprising the step of:

spectrally decomposing the white light impinging on the layer (6) depending on the deformation of the layer (6).

9. A method as claimed in claim 1, further comprising the steps of:

collecting data based on the evaluated changes in the reflected electromagnetic waves for a plurality of test specimens;

coding and storing at least some of the data thus gained on a data carrier such that the data carrier serves as reference for current measurements.

10. An apparatus for determining the spatial structure of a test specimen, comprising: at least one ultrasonic source (3), a body (4) penetrable by ultrasonic waves from the ultrasonic source (3), and a supporting surface (5) located on the body (4) adapted to support the test specimen (2), said supporting surface being arranged at a fixed angle to a beam path of the ultrasonic waves from the ultrasonic source (3), a layer (6) arranged in the body (4), beneath the supporting surface (5) for the test specimen (2), said layer (6) being deformable by ultrasonic waves and reflecting electromagnetic waves, a radiation source (7) which produces electromagnetic waves which are directed toward the layer (6), and at least one detector (8) located in an area of the reflected electromagnetic waves to evaluate changes of said electromagnetic waves caused by the reflection.

11. An apparatus as claimed in claim 10, characterized in that the layer (6) is arranged closely beneath and approximately parallel to the supporting surface (5) and approximately at right angles to the path of the ultrasonic waves.

12. An apparatus as claimed in claim 10, characterized in that the layer (6) is a mirror layer.

13. An apparatus as claimed in claim 10, characterized in that a plurality of ultrasonic wave deformable and electromagnetic wave reflecting layers (6) are provided.

14. An apparatus as claimed in claim 10 characterized in that a plurality of detectors (8) are arranged in a matrix-like manner, the plurality of detectors (8) having a surface which is arranged such that a normal to the surface is approximately parallel to an emergence angle (9) of the electromagnetic waves.

15. An apparatus as claimed in claim 10, characterized in that the at least one ultrasonic source (3) is coupled to at least one pulsar.

16. An apparatus as claimed in claim 10 characterized in that at least one projector lens is arranged in a path of the reflected electromagnetic waves between the body (4) and the at least one detector (8).

17. An apparatus as claimed in claim 10, characterized in that the layer (6) is curved.

* * * * *